United States Patent
Broeckx et al.

(10) Patent No.: US 6,919,459 B2
(45) Date of Patent: Jul. 19, 2005

(54) PROCESS FOR PREPARING BENZIMIDAZOLE-TYPE COMPOUNDS

(76) Inventors: Rudy Laurent Maria Broeckx, Janssen Phamaceutica N.V., Turnhoutseweg 30, B-2340 Beerse (BE); Dirk De Smaele, Janssen Phamaceutica N.V., Turnhoutseweg 30, B-2340 Beerse (BE); Stefan Marcel Herman Leurs, Janssen Phamaceutica N.V., Turnhoutseweg 30, B-2340 Beerse (BE); Filip Verberckmoes, Janssen Phamaceutica N.V., Turnhoutseweg 30, B-2340 Beerse (BE)

( * ) Notice: Subject to any disclaimer, the term of this patent is extended or adjusted under 35 U.S.C. 154(b) by 0 days.

(21) Appl. No.: 10/483,587
(22) PCT Filed: Jul. 9, 2002
(86) PCT No.: PCT/EP02/07693
§ 371 (c)(1), (2), (4) Date: Jun. 4, 2004
(87) PCT Pub. No.: WO03/008406
PCT Pub. Date: Jan. 30, 2003

(65) Prior Publication Data
US 2004/0209918 A1 Oct. 21, 2004

(30) Foreign Application Priority Data
Jul. 16, 2001 (EP) ............................................ 01202696

(51) Int. Cl.$^7$ ............................................. C07D 401/12
(52) U.S. Cl. ..................................................... 546/273.7
(58) Field of Search ...................................... 546/273.7

(56) References Cited

FOREIGN PATENT DOCUMENTS

| WO | WO 91/18895 A1 | 12/1991 |
|----|----------------|---------|
| WO | WO 00/02876 A1 | 1/2000  |

OTHER PUBLICATIONS

Abstract XP002183669 Changzhou No 4 Pharm Plant 1997.

*Primary Examiner*—Patricia L. Morris

(57) ABSTRACT

The present invention relates to an improved process for the preparation of proton pump inhibitors of the benzimidazole-type such as rabeprazole, omeprazole, pantoprazole, lansoprazole and esome prazole, of general formula (1) by oxidation of the corresponding sulfide followed by extraction of the sulfone by-product with an aqueous alkaline solution at controlled pH.

14 Claims, No Drawings

PROCESS FOR PREPARING BENZIMIDAZOLE-TYPE COMPOUNDS

CROSS REFERENCE TO RELATED APPLICATIONS

This application is the national stage of Application No. PCT/EP02/07693, filed Jul. 9, 2002, which application claims priority from EPO Application No. 01202696.9, filed Jul. 16, 2001.

The present invention relates to an improved process for the preparation of proton pump inhibitors of the benzimidazole-type such as rabeprazole, omeprazole, pantoprazole, lansoprazole and esomeprazole.

A benzimidazole-type compound or an alkali metal salt thereof has a strong inhibitory action on the so-called proton pump. In a general sense, they may be used for prevention and treatment of gastric-acid related diseases in mammals and especially in man, including e.g. gastro-oesophageal reflux, gastritis, duodenitis, gastric ulcer and duodenal ulcer.

Proton pump inhibitors of the benzimidazole-type are very susceptible to degradation under acidic or neutral conditions and particular reaction conditions are needed for their preparation. Processes for the preparation of said benzimidazole-type compounds have been disclosed, for instance, in EP-0,005,129, EP-0,066,287, EP-0,174,726, and EP-0,268,956.

The present invention provides an improved process for preparing benzimidazole-type compounds of general formula (I)

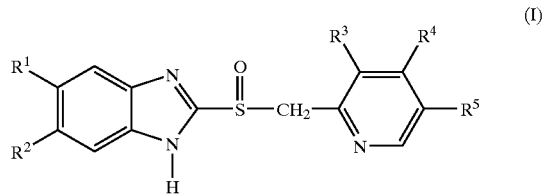

(I)

wherein $R^1$ and $R^2$ are the same as or different from each other and are selected from hydrogen, methoxy or difluoromethoxy, $R^3$, $R^4$ and $R^5$ are the same as or different from each other and are selected from hydrogen, methyl, methoxy, methoxypropoxy or trifluoroethoxy, characterized by the steps of a) reacting a compound of general formula (II)

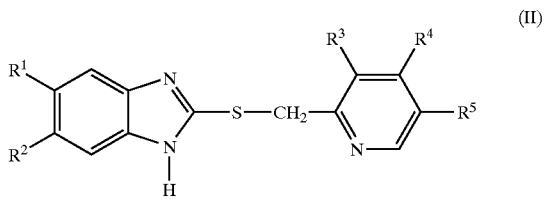

(II)

with an oxidizing agent in a suitable solvent,
b) extracting the reaction mixture with an aqueous alkaline solution with a pH ranging from 9.50 to 12.00 and removing the water layer,
c) extracting the organic layer of the previous step with an aqueous alkaline solution having a pH of 13.00 or higher and removing the organic layer,
d) isolating the compound of formula (I) from the water layer of the previous step.

The term "proton pump inhibitors of the benzimidazole-type", "benzimidazole-type compounds" or "compounds of formula (I)" is meant to include both the neutral form of said compounds and the alkaline salt forms of said compounds. Alkaline salts forms are for instance the $Mg^{2+}$, $Ca^{2+}$, $Na^+$, $K^+$ or $Li^+$ salts, preferably the $Mg^{2+}$ or $Na^+$ salts. Where applicable, the benzimidazole-type compounds of formula (I) include the racemic form, or a substantially pure enantiomer thereof, or alkaline salts of the single enantiomers.

The structural formulae of some of these proton pump inhibitors of the benzimidazole-type are listed below:

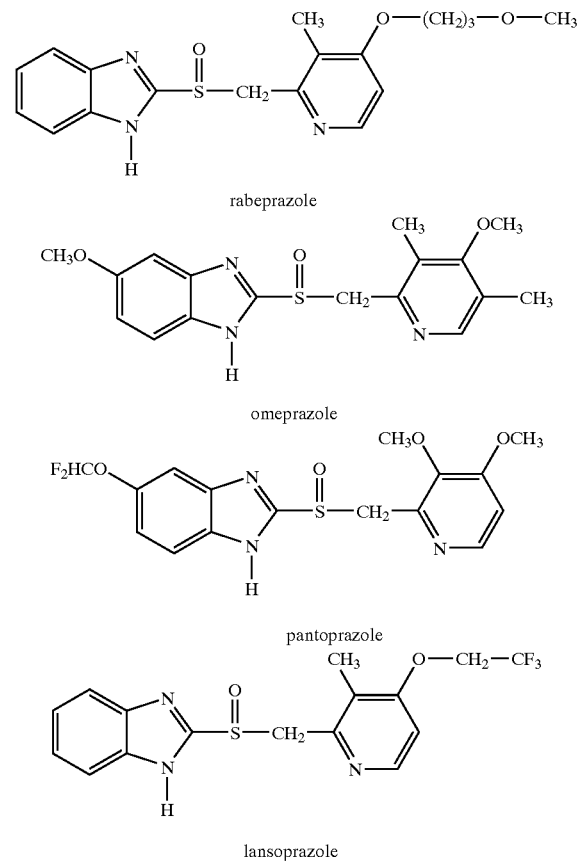

rabeprazole omeprazole pantoprazole lansoprazole

Suitable proton pump inhibitors of the benzimidazole-type are for example disclosed in EP-0,268,956, EP-0,005,129, EP-0,066,287, and EP-0,174,726. EP-0,652,872 discloses esomeprazole, i.e. the magnesium salt of the (−)-enantiomer of omeprazole. Typically, benzimidazole-type compounds of formula (I) are prepared by oxidation of the sulfide intermediates of formula (II) in a suitable solvent.

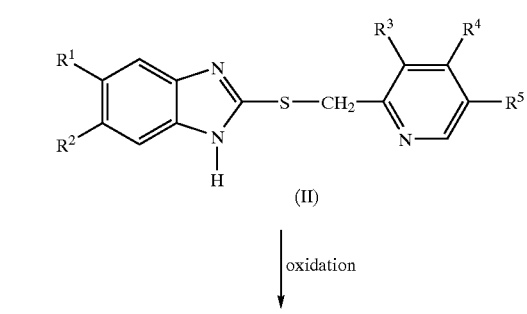

(II)

↓ oxidation

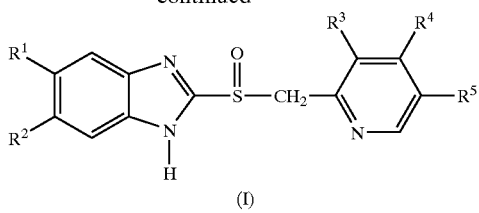

(I)

The oxidation step uses an oxidizing agent such as, m-chloroperoxybenzoic acid, monoperoxyphthalate, hydrogen peroxide (with or without catalysts), permanganates, N-chloro or N-bromo succinimide, 1,3-dibromo-5,5-dimethylhydantoin, 2-hydroperoxyhexafluoro-2-propanol, iodosylbenzene, manganese(III) acetylacetonate, oxygen (with or without catalysts), ozone, peroxy monosulfate, ruthenium tetroxide, perborate, periodate, acyl nitrates, tert-butylhydroperoxide, dimethyl dioxiranes, hypochlorite, cerium ammonium nitrate, 2-nitrobenzenesulfinyl chloride/ potassium superoxide, N-sulfonyloxaziridines, sodium bromite, benzoyl peroxide and the like, in a solvent system consisting of an organic solvent such as, e.g. dichloromethane.

Since proton pump inhibitors of the benzimidazole-type are very susceptible to degradation under acidic or neutral conditions the reaction mixture is usually worked-up under basic conditions. These basic conditions may decompose any unwanted oxidizing agent still present in the reaction mixture and may also neutralise any acid formed when the oxidizing agent is consumed in the oxidation reaction.

The main problem with the oxidation reaction to convert the sulfide intermediates of formula (II) into the sulfoxide compounds of formula (I) is over-oxidation, i.e. oxidation from sulfoxides of formula (I) to sulfones of formula (III).

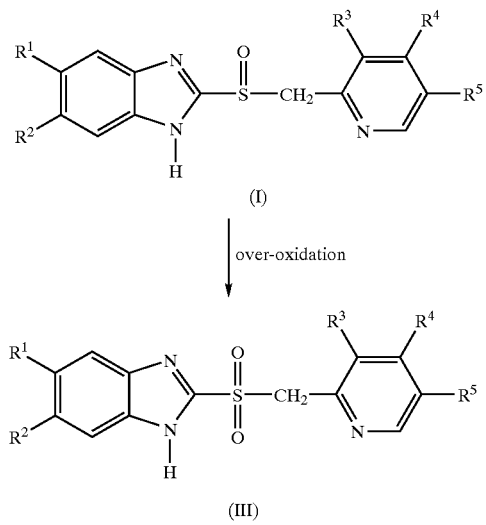

The formation of sulfones of formula (III) due to over-oxidation is almost impossible to avoid and can be kept to a minimum by performing the oxidation reaction at a low temperature and restricting the amount of oxidizing agent. Typically the amount of oxidizing agent is less than 1 molar equivalent of the starting material, i.e. sulfide intermediates of formula (II), which inevitably results in a less than 100% conversion of starting material. Usually the amount of oxidizing agent is a compromise between maximum conversion of starting material, maximum formation of sulfoxides of formula (I) and minimum formation of unwanted sulfones of formula (III).

Furthermore removal of the sulfones of formula (III) has often proved to be difficult, time-consuming and costly, in particular when high performance chromatography on an industrial scale is needed.

The object of the present invention is to provide an improved method for the synthesis of benzimidazole-type compounds of formula (I), which is more convenient and more efficient than the previously known methods.

The present invention achieves this object by providing an improved process for preparing benzimidazole-type compounds of general formula (I) which is characterized by the steps of a) reacting a compound of general formula (II)

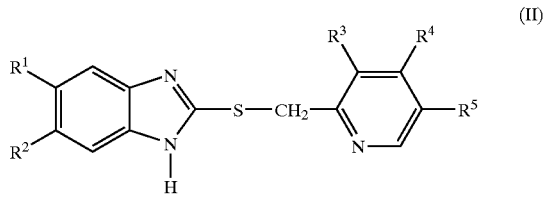

with an oxidizing agent in a suitable solvent, b) extracting the reaction mixture with an aqueous alkaline solution with a pH ranging from 9.50 to 12.00 and removing the water layer, c) extracting the organic layer of the previous step with an aqueous alkaline solution having a pH of 13.00 or higher and removing the organic layer, d) isolating the compound of formula (I) from the water layer of the previous step.

This improved process has the advantage that the first extraction step b) removes any formed sulfones of formula (III) and the second extraction step c) removes any unreacted sulfides of formula (II) whereby the water layer in step d) only contains the desired benzimidazole-type compounds of formula (I) which can be easily purified to the level required for pharmaceutical preparations.

A further advantage of the improved process is that higher amounts of oxidizing agent can be used, giving a higher yield of the desired compounds of formula (I) and fewer unreacted sulfides of formula (II), since any formed undesired sulfones of formula (III) are easily removed by the first extraction step thereby making further purification of the isolated sulfoxides of formula (I) much more easy.

The oxidizing agent used in the above described improved process can be m-chloroperoxybenzoic acid, monoperoxyphthalate, hydrogen peroxide (with or without catalysts), permanganates, N-chloro or N-bromo succinimide, 1,3-dibromo-5,5-dimethylhydantoin, 2-hydroperoxyhexafluoro-2-propanol, iodosylbenzene, manganese(III) acetylacetonate, oxygen (with or without catalysts), ozone, peroxy monosulfate, ruthenium tetroxide, perborate, periodate, acyl nitrates, tert-butylhydroperoxide, dimethyl dioxiranes, hypochlorite, cerium ammonium nitrate, 2-nitrobenzenesulfinyl chloride/potassium superoxide, N-sulfonyloxaziridines, sodium bromite, benzoyl peroxide or any other oxidizing agent suitable for oxidising sulfides of formula (II). Preferably m-chloroperoxybenzoic acid is used. Said oxidizing agent is suitably used in an amount of 0.5 to 2.0 molar equivalents of starting material, i.e. sulfides of formula (II). The optimal amount of oxidizing agent depends on the type of oxidizing agent used, the specific sulfide of formula (II) and further reaction conditions such as solvent and temperature, and can easily be determined by the skilled person.

The aqueous alkaline solution in the first and second extraction step can be any aqueous solution of an inorganic base, such as sodium hydroxide, potassium hydroxide, sodium carbonate and the like; or any aqueous solution of an organic base such as aqueous ammonia and the like.

The pH of the first extraction step generally ranges from 9.50 to 12.00 and preferably from 10.50 to 11.50. When the benzimidazole-type compounds of formula (I) is rabeprazole the pH preferably ranges from 10.70 to 11.20, more preferably the pH ranges from 10.85 to 10.95.

The compounds of formula (I) can be isolated from the water layer in step d) for instance by adding an organic solvent, such as, e.g. dichloromethane, to said water layer and lowering the pH whereby said compounds of formula (I) are transferred to the organic layer. Lowering the pH can be done for instance by adding an aqueous ammonium acetate solution. Concentrating said organic layer under vacuum then yields the desired compounds of formula (I).

Particular benzimidazole-type compounds of formula (I) that can be prepared by the improved process of the present invention are rabeprazole, omeprazole, pantoprazole, lansoprazole, and esomeprazole; in particular rabeprazole.

In another aspect, the present invention also provides a process for removing sulfones of formula (III), wherein $R^1$ and $R^2$ are the same as or different from each other and are selected from hydrogen, methoxy or difluoromethoxy, $R^3$, $R^4$ and $R^5$ are the same as or different from each other and are selected from hydrogen, methyl, methoxy, methoxypropoxy or trifluoroethoxy,

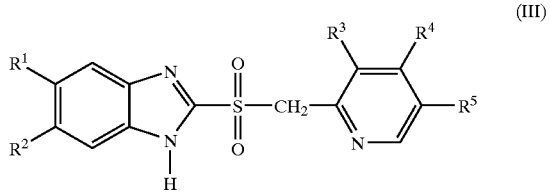

(III)

from a reaction mixture comprising sulfoxides of formula (I), wherein $R^1$ and $R^2$ are the same as or different from each other and are selected from hydrogen, methoxy or difluoromethoxy, $R^3$, $R^4$ and $R^5$ are the same as or different from each other and are selected from hydrogen, methyl, methoxy, methoxypropoxy or trifluoroethoxy,

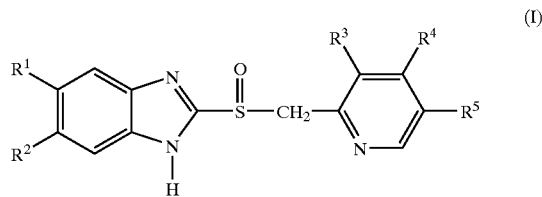

(I)

by extracting the reaction mixture with an aqueous alkaline solution with a pH ranging from 9.50 to 12.00, preferably from 10.50 to 11.50, and removing the water layer and isolating the sulfoxides of formula (I) from the organic layer.

When the sulfoxide of formula (I) is rabeprazole the pH preferably ranges from 10.70 to 11.20, more preferably the pH ranges from 10.85 to 10.95.

A preferred embodiment of said process for removing sulfones of formula (III) is when the sulfoxide of formula (I) is rabeprazole.

The present invention is illustrated below with non-limiting examples.

Experimental Part

In the procedures described hereinafter the following abbreviations were used: "m-CPBA" stands for meta-chloroperoxybenzoic acid, "PTBI" stands for 2-[[[4-(3-methoxypropoxy)-3-methyl-2-pyridinyl]methyl]thio]-1H-benzimidazole, "PPSI" stands for 2-[[[4-(3-methoxypropoxy)-3-methyl-2-pyridinyl]methyl]sulfinyl]-1H-benzimidazole (also known as rabeprazole), and "SUBI" stands for 2-[[[4-(3-methoxypropoxy)-3-methyl-2-pyridinyl]methyl]sulfonyl]-1H-benzimidazole.

EXAMPLE 1

To a solution of PTBI (0.25 mol) in dichloromethane (688 ml), stirred and kept at a temperature of −20° C., a solution of m-CPBA (0.22 mol) in dichloromethane (330 ml) was added over 1 hour while keeping the temperature of the reaction mixture at −20° C. The reaction mixture was stirred at −20° C. for 30 minutes.

First Extraction Step

Water (368 ml) was added to the organic layer and the pH was raised to 10.40 with a NaOH solution (10%). The pH of the reaction mixture was adjusted to pH=10.85 with an aqueous $NH_3$ solution and the water layer was separated from the organic layer.

Second Extraction Step

Water (368 ml) was added to the organic layer and the pH was raised to 13.0 with a NaOH solution (10%). The organic layer was removed and dichloromethane (168 ml) was added to the water layer. While stirring, an aqueous ammonium acetate solution was added to a pH of 10.50. The water layer was removed from the organic layer and the organic layer was concentrated under reduced pressure yielding a residue. Said residue was crystallised from acetone, yielding PPSI (0.143 mol, 57%).

EXAMPLE 2

To a solution of PTBI (0.25 mol) in dichloromethane (688 ml), stirred and kept at a temperature of −20° C., a solution of m-CPBA (0.15 mol) in dichloromethane (360 ml) was added over 1 hour while keeping the temperature of the reaction mixture at −20° C. The reaction mixture was stirred at −20° C. for 30 minutes.

Extraction Step

Water (368 ml) was added to the reaction mixture and the pH was raised to 13.0 with a NaOH solution (10%). The organic layer was removed and dichloromethane (168 ml) was added to the water layer. While stirring, an aqueous ammonium acetate solution was added to a pH of 10.50. The water layer was removed from the organic layer and the organic layer was concentrated under reduced pressure yielding a residue. Said residue was crystallised from acetone, yielding PPSI (0.11 mol, 44%).

Purity of the obtained PPSI was measured using HPLC on a Nucleosil 100 C18 (5 μm, 150 mm×4.6 mm I.D.) column using isocratic elution with a flow rate of 1 ml/minute, a mobile phase consisting of 40% eluent A and 60% eluent B (eluent A is a mixture of 0.05 M $KH_2PO_4$ and 0.05 M $Na_2HPO_4$ with a pH of 7 in a 2:1 (v/v) ratio; eluent B is methanol) and UV detection at 290 nm.

TABLE 1 comparison of reaction parameters (yield of PPSI is determined after crystallisation and is relative to the starting material PTBI)

| | mol equivalent of m-CPBA | yield of PPSI | % of side-product (SUBI) |
|---|---|---|---|
| Example 1 | 0.88 | 57% | ≦0.8% |
| Example 2 | 0.60 | 44% | ≦0.8% |

For use in pharmaceutical preparations PPSI, generally known as rabeprazole, should not contain more than 0.8% of the sulfone SUBI. Hence the use of the first extraction step which removes any formed sulfone from the reaction mixture allows for the use of a higher amount of oxidizing agent, thereby giving a substantially higher yield of PPSI without the need to change the work-up procedure, i.e. crystallisation, to obtain the sulfoxide PPSI containing 0.8% or less of the sulfone SUBI.

EXAMPLE 3

General Oxidation and Extraction Procedure
A. Method A (with Additional Extraction Step for Removing Sulfones of Formula (III))

To a solution of a sulfide intermediate of formula (II) (0.05 mol) in dichloromethane (137.5 ml), stirred and kept at a temperature of −40° C., a solution of m-CPBA (0.92 equivalents or 0.046 mol) in dichloromethane (82.5 ml) was added over 1 hour while keeping the temperature of the reaction mixture at −40° C. The reaction mixture was stirred at −40° C. for 30 minutes.

First Extraction Step

Cooling of the reaction mixture was stopped before the pH was raised to 10.40 with a NaOH solution (10%) and water (75 ml) was added to the organic layer. The pH of the reaction mixture was adjusted to pH=11.10 with an aqueous $NH_3$ solution and the water layer was separated from the organic layer.

Second Extraction Step

Water (75 ml) was added to the organic layer of the previous step and the pH was raised to 13.0 with a NaOH solution (10%). The organic layer was removed and dichloromethane (75 ml) was added to the water layer. While stirring, an aqueous ammonium acetate solution was added to a pH of about 10.44. The water layer was removed from the organic layer and the organic layer was concentrated under reduced pressure yielding a solid residue.

B. Method B (without Additional Extraction Step for Removing Sulfones of Formula (III))

To a solution of a sulfide intermediate of formula (II) (0.05 mol) in dichloromethane (137.5 ml), stirred and kept at a temperature of −40° C., a solution of m-CPBA (0.92 equivalents or 0.046 mol) in dichloromethane (82.5 ml) was added over 1 hour while keeping the temperature of the reaction mixture at −40° C. The reaction mixture was stirred at −40° C. for 30 minutes.

Extraction Step

Cooling of the reaction mixture was stopped before the pH was raised to 13.0 with a NaOH solution (10%) and water (75 ml) was added to the organic layer. The organic layer was removed and dichloromethane (75 ml) was added to the water layer. While stirring, an aqueous ammonium acetate solution was added to a pH of 10.50. The water layer was removed from the organic layer and the organic layer was concentrated under reduced pressure yielding a solid residue.

C. Results

The following Table 3 lists the results for the proton pump inhibitors rabeprazole, omeprazole and lansoprazole prepared both times using Method A (with additional extraction step for removing sulfones of formula (III)), and Method B (without additional extraction step for removing sulfones of formula (III)).

Starting sulfide of formula (II) for the preparation of rabeprazole was 2-[[[(4-(3-methoxypropoxy)-3-methyl-2-pyridinyl]methyl]thio]-1H-benzimidazole. Starting sulfide of formula (II) for the preparation of omeprazole was 5-methoxy-2-[[(4-methoxy-3,5-dimethyl-2-pyridinyl)methyl]thio]-1H-benzimidazole. Starting sulfide of formula (II) for the preparation of lansoprazole was 2-[[[3-methyl-4-(2,2,2-trifluoroethoxy)-2-pyridinyl]methyl]thio]-1H-benzimidazole.

The amount of sulfones of formula (III) and compounds of formula (I) present in the obtained solid residues, prepared according to Method A or Method B, was measured using HPLC on a Nucleosil 100 C18 (5 μm, 150 mm×4.6 mm I.D.) column using isocratic elution with a flow rate of 1 ml/minute, a mobile phase consisting of 40% eluent A and 60% eluent B (eluent A is a mixture of 0.05 M $KH_2PO_4$ and 0.05 M $Na_2HPO_4$ with a pH of 7 in a 2:1 (v/v) ratio; eluent B is methanol) and UV detection at 290 nm. Standard deviation is less than 5%.

TABLE 3 amount of sulfones of formula (III) and compounds of formula (I) present in the obtained solid residues

| Rabeprazole | % sulfon in residue | % rabeprazole in residue |
|---|---|---|
| Method A | 0.33 | 92.5 |
| Method B | 0.78 | 90.4 |
| Omeprazole | % sulfon in residue | % omeprazole in residue |
| Method A | 0.26 | 99.4 |
| Method B | 0.53 | 100.5 |
| Lansoprozole | % sulfon in residue | % lansoprazole in residue |
| Method A | 4.1 | 100.5 |
| Method B | 11.3 | 97.8 |

What is claimed is:

1. An process for preparing benzimidazole-type compounds of general formula (I)

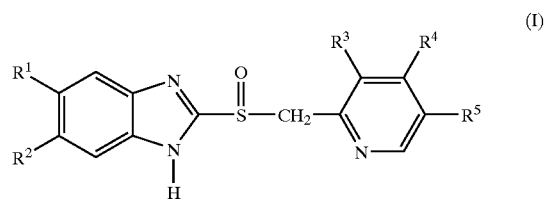

wherein $R^1$ and $R^2$ are the same as or different from each other and are selected from hydrogen, methoxy or difluoromethoxy, $R^3$, $R^4$ and $R^5$ are the same as or different from each other and are selected from hydrogen, methyl, methoxy, methoxypropoxy or trifluoroethoxy, characterized by the steps of a) reacting a compound of general formula (II)

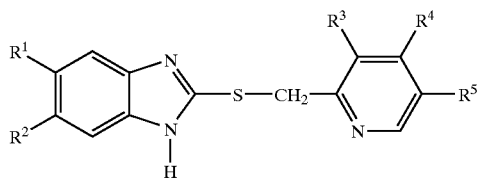

(II)

with an oxidizing agent in a suitable solvent, b) extracting the reaction mixture with an aqueous alkaline solution with a pH ranging from 9.50 to 12.00 and removing the water layer, c) extracting the organic layer of the previous step with an aqueous alkaline solution having a pH of 13.0 or higher and removing the organic layer, d) isolating the compound of formula (I) from the water layer of the previous step.

2. A process as claimed in claim 1 wherein the pH of the first extraction step b) ranges from 10.50 to 11.50.

3. A process as claimed in claim 1 wherein the oxidizing agent is selected from m-chloroperoxybenzoic acid, monoperoxyphthalate, hydrogen peroxide (with or without catalysts), permanganates, N-chloro or N-bromo succinimide, 1,3-dibromo-5,5-dimethylhydantoin, 2-hydroperoxyhexafluoro-2-propanol, iodosylbenzene, manganese(III) acetylacetonate, oxygen (with or without catalysts), ozone, peroxy monosulfate, ruthenium tetroxide, perborate, periodate, acyl nitrates, tert-butylhydroperoxide, dimethyl dioxiranes, hypochlorite, cerium ammonium nitrate, 2-nitrobenzenesulfinyl chloride/potassium superoxide, N-sulfonyloxaziridines, sodium bromite, or benzoyl peroxide.

4. A process as claimed in claim 3 wherein the oxidizing agent is m-chloroperoxybenzoic acid.

5. A process as claimed in claim 1 wherein the benzimidazole-type compounds of formula (I) is selected from rabeprazole, omeprazole, pantoprazole, lansoprazole, and esomeprazole.

6. A process as claimed in claim 5 wherein the benzimidazole-type compounds of formula (I) is rabeprazole.

7. A process as claimed in claim 6 wherein the pH of the first extraction step b) ranges from 10.70 to 11.20.

8. A process for removing sulfones of formula (III), wherein $R^1$ and $R^2$ are the same as or different from each other and are selected from hydrogen, methoxy or difluoromethoxy, $R^3$, $R^4$ and $R^5$ are the same as or different from each other and are selected from hydrogen, methyl, methoxy, methoxypropoxy or trifluoroethoxy,

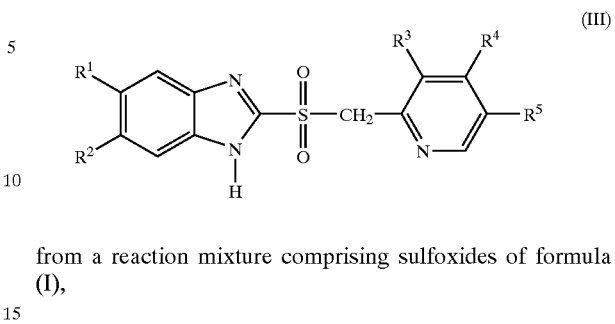

(III)

from a reaction mixture comprising sulfoxides of formula (I),

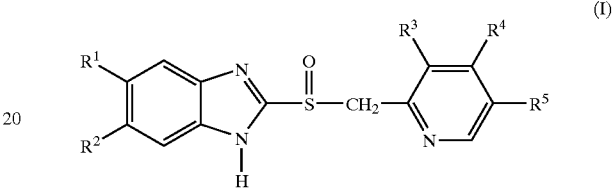

(I)

by extracting the reaction mixture with an aqueous alkaline solution with a pH ranging from 9.50 to 12.00, removing the water layer and isolating the sulfoxides of formula (I) from the organic layer.

9. A process as claimed in claim 8 wherein the pH of the extraction step ranges from 10.50 to 11.50.

10. A process as claimed in claim 8 wherein the sulfoxide of formula (I) is rabeprazole.

11. A process as claimed in claim 9 wherein the sulfoxide of formula (I) is rabeprazole.

12. A process as claimed in claim 6 wherein the pH of the first extraction step b) ranges from 10.85 to 10.95.

13. A process as claimed in claim 2 wherein the oxidizing agent is selected from m-chloroperoxybenzoic acid, monoperoxyphthalate, hydrogen peroxide (with or without catalysts), permanganates, N-chloro or N-bromo succinimide, 1,3-dibromo-5,5-dimethylhydantoin, 2-hydroperoxyhexafluoro-2-propanol, iodosylbenzene, manganese(III) acetylacetonate, oxygen (with or without catalysts), ozone, peroxy monosulfate, ruthenium tetroxide, perborate, periodate, acyl nitrates, tert-butylhydroperoxide, dimethyl dioxiranes, hypochlorite, cerium ammonium nitrate, 2-nitrobenzenesulfinyl chloride/potassium superoxide, N-sulfonyloxaziridines, sodium bromite, or benzoyl peroxide.

14. A process as claimed in claim 13 wherein the benzimidazole-type compounds of formula (I) is rabeprazole.

* * * * *